United States Patent
Thomas et al.

[19]

[11] Patent Number: 5,925,056
[45] Date of Patent: Jul. 20, 1999

[54] SURGICAL CUTTING DEVICE REMOVABLY CONNECTED TO A ROTARY DRIVE ELEMENT

[75] Inventors: James Cooper Thomas, Las Vegas, Nev.; Rick D. Roberts, Moorpark, Calif.

[73] Assignee: Surgical Dynamics, Inc., Norwalk, Conn.

[21] Appl. No.: 08/853,065

[22] Filed: May 8, 1997

Related U.S. Application Data

[63] Continuation-in-part of application No. 08/695,984, Aug. 15, 1996, abandoned
[60] Provisional application No. 60/015,390, Apr. 12, 1996.

[51] Int. Cl.[6] .................................................. A61B 17/14
[52] U.S. Cl. ............................................ 606/180; 606/170
[58] Field of Search .................................... 606/159, 167, 606/170, 171, 180, 160; 604/22

[56] References Cited

U.S. PATENT DOCUMENTS

| | | |
|---|---|---|
| 2,082,982 | 6/1937 | Schumacher . |
| 2,505,917 | 5/1950 | Schumacher . |
| 2,601,513 | 6/1952 | Gladstone . |
| 2,876,777 | 3/1959 | Kees, Jr. . |
| 3,502,082 | 3/1970 | Chatfield . |
| 3,635,222 | 1/1972 | Robinson . |
| 3,688,407 | 9/1972 | Paquette . |
| 4,043,322 | 8/1977 | Robinson . |
| 4,311,140 | 1/1982 | Bridgman . |
| 4,728,319 | 3/1988 | Masch . |
| 4,763,414 | 8/1988 | McNeill, II . |
| 4,887,613 | 12/1989 | Farr et al. . |
| 5,112,345 | 5/1992 | Farr . |
| 5,122,134 | 6/1992 | Borzone et al. . |
| 5,176,693 | 1/1993 | Pannek, Jr. . |
| 5,192,291 | 3/1993 | Pannek, Jr. . |
| 5,222,965 | 6/1993 | Haughton .............................. 606/159 |
| 5,224,945 | 7/1993 | Pannek, Jr. . |
| 5,250,061 | 10/1993 | Michelson . |
| 5,269,787 | 12/1993 | Cozean, Jr. et al. . |
| 5,282,816 | 2/1994 | Miller et al. . |
| 5,366,468 | 11/1994 | Fucci et al. . |
| 5,376,100 | 12/1994 | Lefebvre . |
| 5,456,689 | 10/1995 | Kresch et al. ........................ 606/170 |
| 5,474,532 | 12/1995 | Steppe . |
| 5,509,923 | 4/1996 | Middleman et al. .................. 606/170 |
| 5,556,408 | 9/1996 | Farhat . |
| 5,571,122 | 11/1996 | Kelly et al. ............................ 606/159 |
| 5,613,972 | 3/1997 | Lee et al. . |
| 5,632,756 | 5/1997 | Kruglick . |

FOREIGN PATENT DOCUMENTS

WO 90/02524  3/1990  European Pat. Off. .

*Primary Examiner*—Michael Buiz
*Assistant Examiner*—Kevin Truong

[57] ABSTRACT

A cutting device for the cutting and reduction of matter from a surgical site having a cutting head having an entry tip and a cutting blade positioned on opposed leading edges of a window formed through the interior of the cutting head. The window includes angled walls extending from each cutting blade along the circumference of the window. The cutting head is attached to a shaft for mounting the cutting device to a rotary surgical drill. The cutting head can also have a blade on the outer perimeter of the head. The matter is removed and further reduced as the cutting head is rotated at the surgical site. The geometry of the cutting head and entry tip can be varied for particular surgical procedures. The cutting device can also include a cannula or drill guard.

38 Claims, 8 Drawing Sheets

SURGICAL CUTTING DEVICE REMOVABLY CONNECTED TO A ROTARY DRIVE ELEMENT

CROSS-REFERENCE TO RELATED APPLICATIONS

This application is a continuation-in-part of applicant's U.S. patent application Ser. No. 08/695,984 filed Aug. 15, 1996, now abandonment which claims priority from U.S. Provisional Application No. 60/015,390 filed Apr. 12, 1996 now pending.

BACKGROUND OF THE INVENTION

This invention relates generally to devices used in surgical procedures, such as, for example, endoscopic diskectomy and endoscopic spinal fusion. More specifically, the invention relates to a rotatable surgical cutting device which is removably connected to a rotary drive element.

FIELD OF THE INVENTION

In the United States, spinal disk problems are the most common cause of disability of people under 45 years of age. There are currently 5.2 million Americans either temporarily or permanently disabled as a result of chronic back pain. Approximately 220,000 spinal operations are performed in America each year to combat the disabilities caused by spinal disk problems.

A common problem among patients suffering from chronic back pain is a protruding lumbar intervertebral disc. This condition occurs when a portion of the disk protrudes into the spinal canal space and creates pressure on a nerve. A patient may also experience a partial or complete collapse of an intervertebral disk, resulting in spinal instability, immobility and severe chronic pain.

It is often necessary to surgically remove offending disk material from the spinal canal to improve the spinal function of the patient and to relieve chronic pain. In some cases it is also necessary to perform a spinal fusion, to improve spinal stability and to provide additional support for any damaged intervertebral disk. Also more recently, metal bone cages that are placed between intervertebral bodies have begun to be utilized to improve the stability of the spine both during and after the fusion healing process.

Procedures such as endoscopic diskectomy can be used for the removal of fibrous intervertebral tissue. Endoscopic surgeries are accomplished by creating small openings or "ports" in the body, through which various small instruments or a camera may be inserted and manipulated to observe or work in the disk space area. Current endoscopic procedures utilized for the removal of disk material rely primarily upon automated or manual methods. (Surgical Dynamics Nucleotome or the Soframor-Danek Diskector). These methods remove intervertebral disk material by using a guillotine cutting blade, with the aspiration of disk material into a port connected to a cannula, once the device is activated.

For open spinal fusions, products currently available for the removal of intervertebral disk tissue include the Acromed manual PLIG instrumentation and the Cloward PLIF set instrumentation. These instruments are manual in operation and utilize rasps and rongeurs, whereby disk material is removed by increasing the size of the rasp sequentially. Devices currently used for the preparation of the intervertebral disk space for bone cage placement are also manual in operation, utilizing a traditional drill bit and brace or drill bit handle configuration.

Based upon the current instrumentation and procedures available for the removal of intervertebral disk material and the preparation of bone graft sites and bone cage placement, there remains an opportunity to improve the speed, accuracy and effectiveness of these procedures. In addition, with the recent introduction of the bone c(age technology, it is far more desirable to have the capacity to generate a circular void in the intervertebral disk space for the placement of the bone cage rather than a void that is square, rectangular or cruciate in shape. Furthermore, animal studies have indicated that circular holes in the intervertebral disk space provide an improved response to healing over those that are square, rectangular, or cruciate in shape. Therefore, an opportunity exists for the introduction of a device that will provide a smooth circular void in the intervertebral disk space in preparation for bone cage placement and allowing for improved healing of the annular opening.

Also due to the tenacious adhesion of the disk material to the vertebral end plate, an opportunity exists for a more efficient and effective method of removing disk material from this area of the vertebra in preparation for bone grafts.

Lastly, there remains an opportunity to reduce the amount of trauma suffered by the patient during back surgery, as the result of instrument movement and manipulation in and around the spinal canal and surrounding pathology.

SUMMARY OF THE INVENTION

The invention is a surgical cutting device constructed from one piece of hardened surgical steel. Alternatively the cutting device can be constructed of multiple parts braised or welded together. The device has a proximal end comprising a mounting shaft, a main shaft, and optional depth indicators located on the main shaft. The device also includes a cutting head positioned at the end of the main shaft at the distal end of the device.

The mounting shaft is designed to fit into most standard low or high speed rotary surgical drills. The cutting device is attached to and removable from the rotary drill in the same manner as currently available rotary tools and accessories, namely by placing the mounting shaft into the friction lock collet of the drill. The main shaft of the cutting device is designed in various lengths to enable the use of the device for both cannulated endoscopic surgeries, or noncannulated open back surgeries. The main shaft can be a straight cylindrical shaft or can be threaded similar to a screw which serves to move displaced emulsified disk material from the tip of the cutting device. The optional depth indicators provide a method for the instantaneous observation of cutting depth when the device is in the intervertebral disk space. These indicators also serve to alert the surgeon to over-penetration into the disk wall.

The cutting head of the device includes two cutting blades and an entry tip. The two bladed configuration of the cutting head forms a window between the cutting blades providing an area for removed disk material to accumulate and be further reduced in density.

The cutting head of the device is designed with various outside diameters and tip configurations. The various head diameters allow for the device to be used for the removal of disk material in the cervical, thoracic or lumbar regions of the spine, based upon the pathology and intervertebral disk space of the patient. The unique design of the head enables the smooth and accurate entry of the device into the intervertebral disk space, while simultaneously cutting and reducing the density of the removed intervertebral fibro cartilaginous disc material. The head of the device is also designed to perform decortication of bone if desired, either simultaneously or independently to the removal of the disk material. Based upon the requirements of the surgical procedure, the surgeon may select one or more of the various tip configurations to perform the disk removal procedure. Also, by using a series of incrementally increasing diameter heads, the surgeon can accurately increase the size of the void created in the intervertebral disk space. This provides an evacuated disk space in preparation for a bone graft or the placement of bone cage devices.

The head configurations of the device can be round, teardrop, bulb, or elliptical shaped or modified versions thereof, or notched or flame shaped. The various head configurations include one of a number of different entry tip configurations including a flat ended arrow style tip, a conical bullet style tip, an elliptical, circular, or rounded tip and modified versions thereof. The cutting tip may also include an additional cutting blade or blades to facilitate removal of tissue. These additional cutting blades can be a single blade, multiple blades, a raised spiral flute or helix circling the diameter of the head, or a rasp configuration.

The bullet and arrow style tips are designed to be used primarily for the initial entry into the intervertebral disk space. These tips provide a smooth entry into the annulus of the disk, to begin the intervertebral disk tissue removal process. The rounded tip is designed primarily to be used in a secondary operation, to increase the amount of disk material removed and to provide a smooth circular void in the disk. The tips of the devices may also be used for the decortication of bone if desired. Based upon the procedure to be performed, the location of the injury and the position of the offending disk tissue, the surgeon will select the device head configuration, entry tip style and diameter accordingly.

The device may be used in a cannulated or non-cannulated fashion, based upon the surgical procedure to be performed. For an endoscopic surgical procedure, the device is used in a cannulated fashion using a standard surgical cannula and elongated guard that is designed to fit in most surgical cannulas currently available. When used in a cannulated fashion, single, multiple or full length bushings or bearings can be positioned on the shaft of the device to reduce the friction between the shaft and the cannula or guard. A mechanical depth stop can also be incorporated onto the shaft to protect the device from extending too far from the end of the cannula or guard when in use. The cutting device can be made to be removable from or captive within the cannula or surgical guard.

In the case of endoscopic surgeries, the device is placed through the skin and docked on the edge of the intervertebral disc. Once docked, the surgeon uses the surgical drill to rotate the head of the device to smoothly enter the annulus of the disc. As the device enters into the disk space, the disk tissue is cut and migrates to the elliptical opening at ihe center of the cutting head. As the procedure continues, the removed disk material is then further reduced in density, as a result of the spinning of the cutting blades.

The surgeon may then use the device to decorticate the vertebral end plate in preparation for a bone graft, using the same, or a different device diameter or tip configuration. Due to the reduction in density of the removed disk material, normal surgical irrigation and suction can be used to thoroughly flush the surgical site. Since the density of the disk material is reduced to an emulsion, rather than being trimmed or cut into fragments, the possibility of disk debris being left at the operation site is significantly reduced.

When used in open back surgery, the device is used in a non-cannulated fashion, utilizing a guard. In the case of these surgeries, the device is used to remove disk tissue and decorticate bone externally from the cannula, in the same manner as described above for endoscopic procedures.

In addition to spinal related surgeries, the surgical cutting device of the present invention is also applicable to other surgical procedures. For example, in hip surgery, the device can be used for the removal of soft tissue and the decortication of bone. In hip joint revision surgery, the device can be used for the removal of soft tissue, the decortication of bone and the removal of bone cement. In shoulder and shoulder joint replacement surgery, the device is also applicable for the removal of soft tissue and the decortication of bone. In knee surgery and knee joint replacement surgery, the device can also be used for the removal of soft tissue and the decortication of bone. In all types of surgeries, the device will be attached to a rotary drill and operate similarly to that in spinal surgery.

Additional procedures for which the device may be used include, but are not limited to, the micro lumbar laminectomy, the anterior or posterior inter-body lumbar diskectomy and fusion, the cervical anterior diskectomy and fusion and the anterior thoracic diskectomy and fusion and the placement of bone cage devices between intervertebral bodies.

Accordingly, some objectives of this invention are to provide a surgical cutting device capable of providing a circular hole in the intervertebral disk space for efficient disk removal during diskectomies and in preparation for bone grafting and placement of bone cages; provide a surgical device with the ability to accurately remove and reduce the density of intervertebral fibro cartilaginous disk material, and therefore reduce the possibility of disk debris being left in the intervertebral space. This removal of disk material improves bone graft contact and will improve fusion potential; and to minimize the degree of tissue trauma, by reducing the elapsed time and tool manipulation currently required to remove disk material and to prepare a site for bone grafting.

Additional advantages of the present invention will also become apparent from the accompanying detailed description and drawings.

BRIEF DESCRIPTION OF THE DRAWINGS

FIG. 21b is a side view of the cutting device of FIG. 21a;

DETAILED DESCRIPTION

Figure 1:
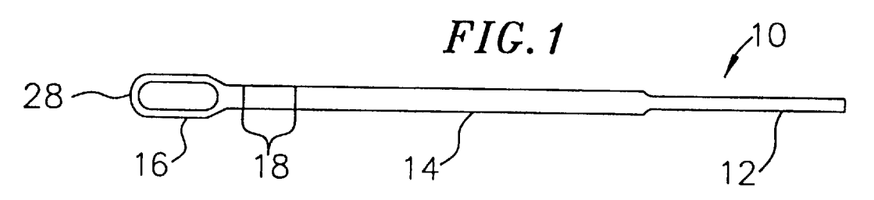
FIG. 1 is a top view of a typical cutting device.
Figure 2:
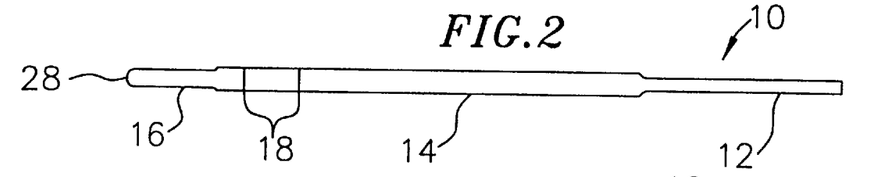
FIG. 2 is a side view of the cutting device of FIG. 1.

Referring to FIGS. 1 and 2, the surgical cutting device 110 of the present invention is shown. The surgical cutting device comprises a mounting shaft 12, a main shaft 14 attached to the mounting shaft, and a cutting head 16 positioned at the opposite end of main shaft 14. The main shaft can include optional engraved depth indicators 18 positioned adjacent to the cutting head. Although the cutting device functions properly without the depth indicators, they do add a certain degree of visualization during surgery. The cutting head, main shaft, and mounting shaft are an integral piece of hardened surgical steel, wherein the mounting shaft is connected to a rotary drill so that the cutting device can be rotated allowing the cutting head to operate. Alternatively, since the cutting head, main shaft, and mounting shaft are of different diameters, the components can be milled from different diameter rod stock and then braised or welded together through a socket or butt joint. Milling from different diameter rod stock is a more efficient use of rod stock which reduces waste and provides an easier milling process for mass production.

Figure 3:
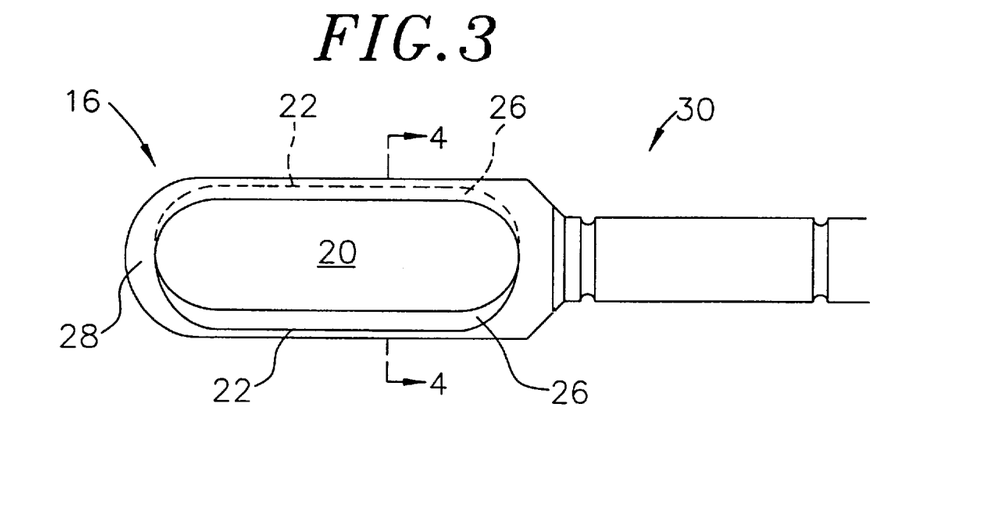
FIG. 3 is a partial detail view of the cutting device of FIG. 1 illustrating the cutting head, including the angled blade configuration and the entry tip.
Figure 4:
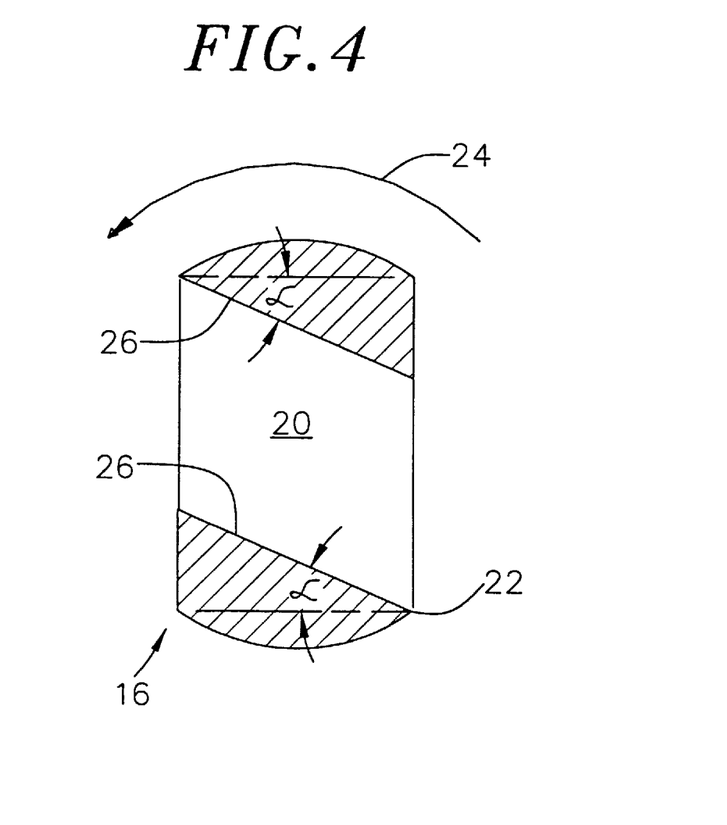
FIG. 4 is a cross-sectional view of the cutting head taken along line 4—4 of FIG. 3.

Referring to FIGS. 3 and 4, the components of the cutting head 16 are shown in greater detail. The cutting head includes a window 20 machined through the cutting head defining two cutting blades 22 on a leading edge of the cutting head as the cutting device is rotated in a counter-clockwise direction 24. Window 20 is machined through the cutting head defining angled walls 26 through the depth of the cutting head. Walls 26 are at an angle a approximately 15–30° from a horizontal plane extending perpendicular to the opening of the window. The cutting blades can be smooth as shown in FIG. 3 or serrated. Window 20 provides an area for removed tissue to accumulate and be further reduced in density, due to the rotation of the cutting blades. The removed material is essentially liquefied and removed by aspiration. It is to be understood that for a cutting device rotatable in a clockwise direction, the configuration of the cutting blades and tapered walls would be a mirror image of that depicted in FIG. 4. The window 20 as shown in FIGS. 1–4 is elliptical or oval in shape, however, other shaped windows are contemplated as discussed subsequently herein. It is to be understood that all cutting head versions disclosed herein include a window defining two cutting blades as shown in FIGS. 3 and 4.

Figures 5, 6:
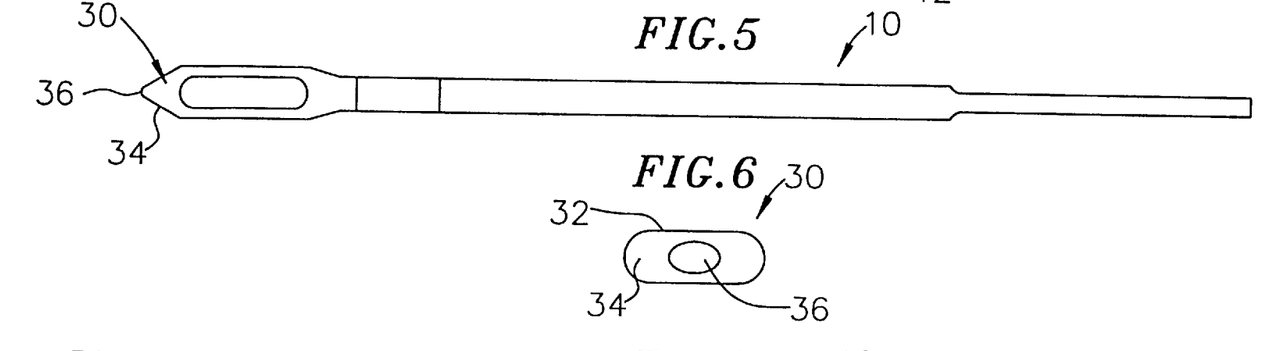
FIG. 5 is a top view of a cutting device having an arrow style entry tip configuration.
FIG. 6 is an end view of the cutting device of FIG. 5.
Figure 7:
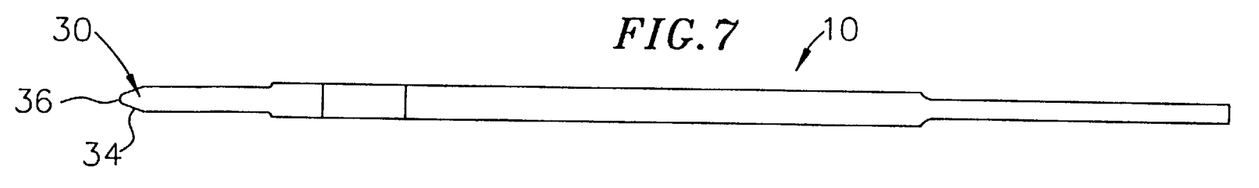
FIG. 7 is a side view of the cutting device of FIG. 5.
Figures 8, 9:
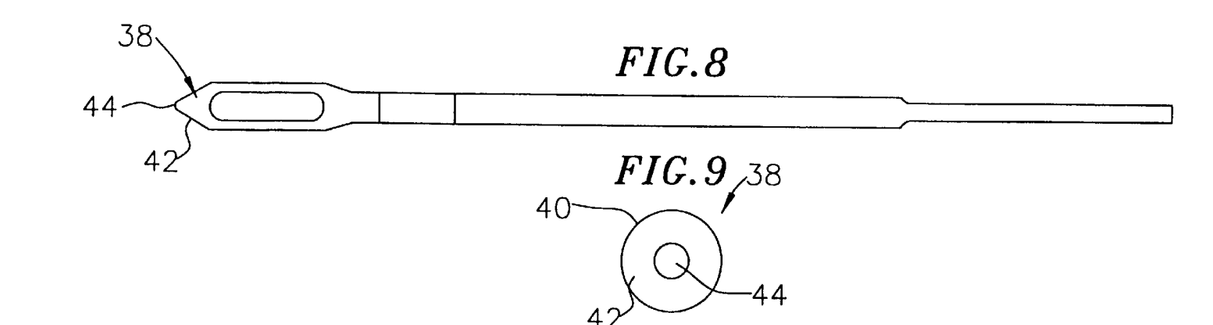
FIG. 8 is a top view of a cutting device having a bullet style entry tip configuration.
FIG. 9 is an end view of the cutting device of FIG. 8.
Figures 10, 11, 12:
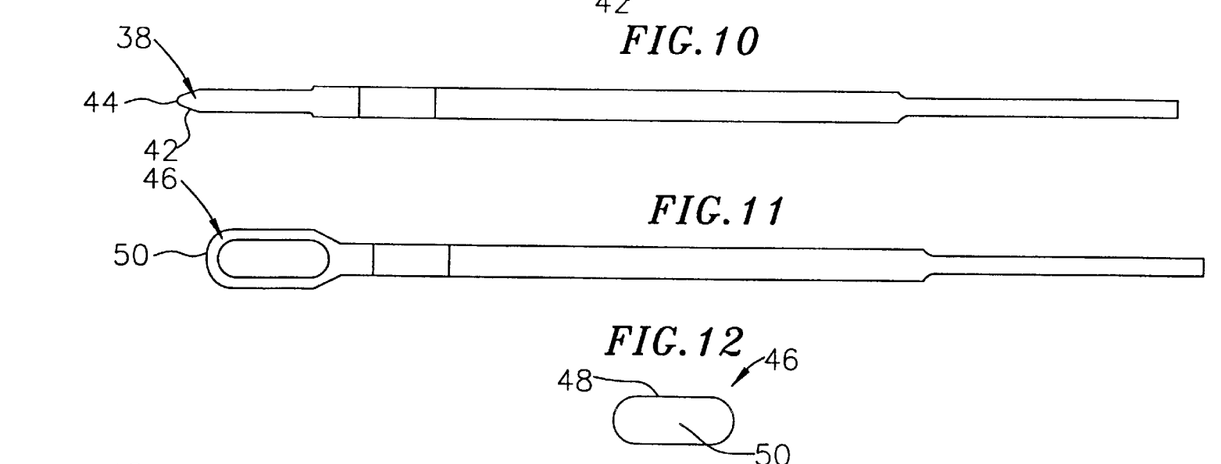
FIG. 10 is a side view of the cutting device of FIG. 8.
FIG. 11 is a top view of a cutting device having a elliptical style entry tip configuration.
FIG. 12 is an end view of the cutting device of FIG. 11.

Another important aspect of the cutting head is the entry tip configuration 28. FIGS. 5–7 illustrate an arrow style entry tip 30 for the cutting device 10. The arrow style entry tip has an elliptical perimeter 32 with a converging sloping surface 34 which converges in a rounded point 36. FIGS. 8–10 illustrate an alternative entry tip configuration being a bullet style entry tip 38. The bullet style entry tip includes a circular outer perimeter 40 having a sloping converging surface 42 terminating in a rounded point 44.

Figure 13:
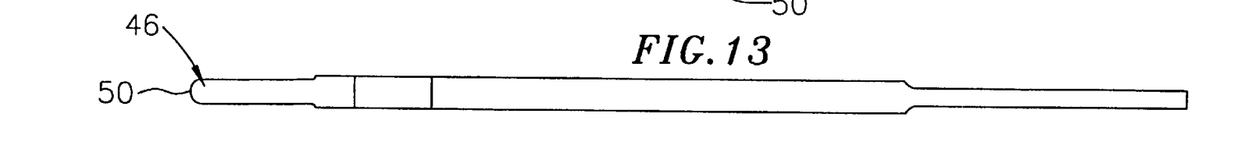
FIG. 13 is a side view of the cutting device of FIG. 11.

FIGS. 11–13 illustrate a second alternative entry tip configuration being an elliptical style entry tip 46. Elliptical style entry tip 46 includes an elliptical perimeter 48 with an arcuate rounded outer surface 50.

The cutting device of the present invention has dimensions that are practical for entry into the spinal intervertebral disc space for the various regions of the spine. The typical outside diameter or width of the cutting head will range from about 3 to about 13 millimeters. Widths of the cutting head can also range from about 5 to about 9 millimeters. The cutting head is balanced around the axis of the device so that the device will not wobble during rotation.

Figure 14:
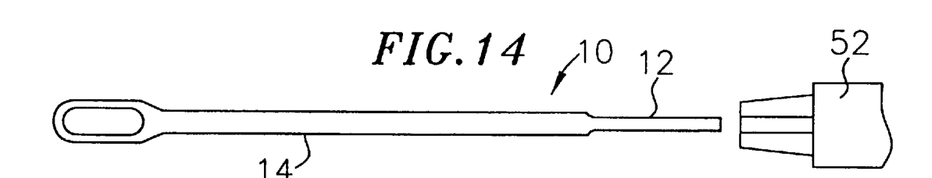
FIG. 14 is a top view of the cutting device of FIG. 1 illustrating the approximate length of the device for use in a non-cannulated open back surgical procedure.

As seen best in FIG. 14, the typical length of the cutting device 10 of the present invention for use in a non-cannulated fashion is from about 3 inches to about 6 inches. This length provides the necessary shaft length for insertion into a surgical drill and drill guard. The mounting shaft 12 of the cutting device has a reduced diameter from the main shaft 14 for insertion into the surgical drill collet 52.

Figure 15:
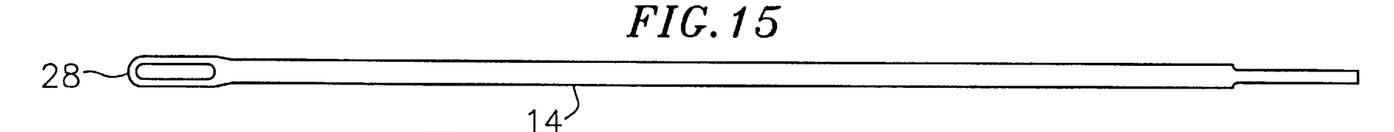
FIG. 15 is a top view of the cutting device of FIG. 1 illustrating the relational length of the device for use in a cannulated endoscopic surgical procedure.

FIG. 15 illustrates the typical length of the cutting device for use in a cannulated, endoscopic fashion and is from about 8 inches to about 12 inches. This length provides the necessary main shaft 14 length for insertion into the surgical drill, a standard surgical cannula and an elongated guard (see FIG. 26) and provides the necessary extension of the entry tip 28 from the cannula for entry into the intervertebral disc. The outside diameter of the cannulated endoscopic device is that necessary to fit in close tolerance with the inside diameter of a standard guard or surgical cannula.

The length of all embodiments of the cutting device of the present invention typically could increase in increments of ½ inch. The mounting shaft diameter 12 typically would be 0.092 inches or 0.125 inches based upon currently available surgical drill mounting collets 52.

Figure 17A:
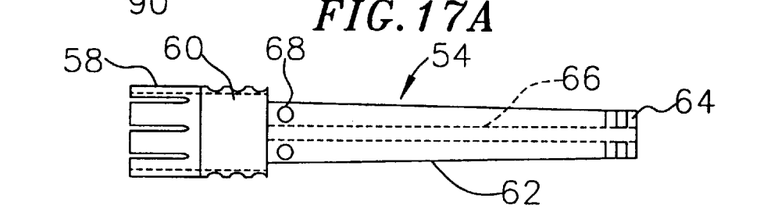
FIG. 17a is a side view of a drill guard for use in an open back surgical procedure.
Figure 17B:
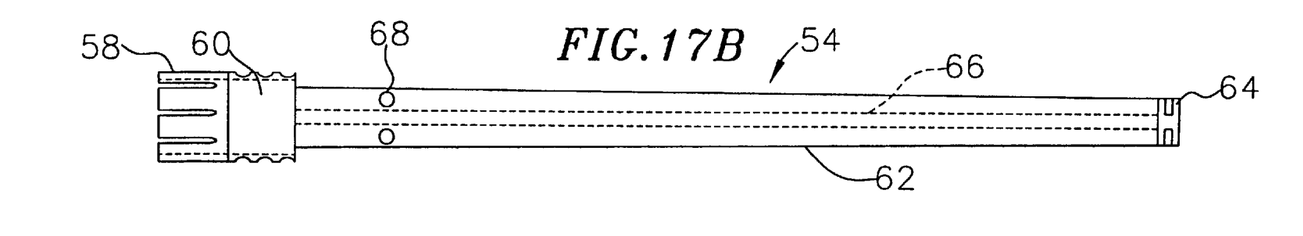
FIG. 17b is a side view of a drill guard for use in an endoscopic surgical procedure.

FIGS. 17a and 17b illustrate standard surgical drill guards, wherein FIG. 17a depicts an open back surgery drill guard 54 and FIG. 17b depicts an endoscopic surgery drill guard 56. The difference between drill guards 54 and 56 is the overall length of the guard. Guards 54 and 56 are made of surgical steel tubing that slides onto the collet 52 of the drill and is held in place by friction. More specifically, guards 54 and 56 include a friction sleeve 58 which slides over the drill collet 52. Drill guards 54 and 56 further include a finger pull 60 for insertion and removal of the drill guard and a guard body 62 extending from the finger pull 60. A stabilizer bushing 64 is positioned at the end of the guard body 62. A shaft opening 66 extends along the length of the guard for insertion of the cutting device. Vent holes 68 are typically located along the length of the guard body 72 at given intervals. Standard commercially available guards or custom made guards that are slightly longer and have a slightly larger internal diameter may be used with the cutting device of the present invention.

Figure 18:
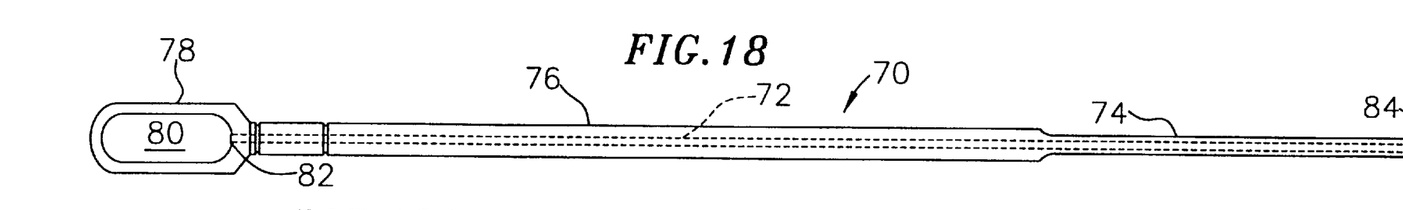
FIG. 18 is a side view of a self-aspirating embodiment of the cutting device of FIG. 1.

FIG. 18 illustrates a self-aspirating cutting device 70 which includes an aspiration channel 72 extending along the length of the mounting shaft 74, main shaft 76 and terminating at window 80 in cutting head 78. The aspiration channel terminates in openings 82 and 84, in the window of the cutting head and in the mounting shaft, respectively. The aspiration channel of the cutting device is for aspiration of the removed material.

Figure 16:
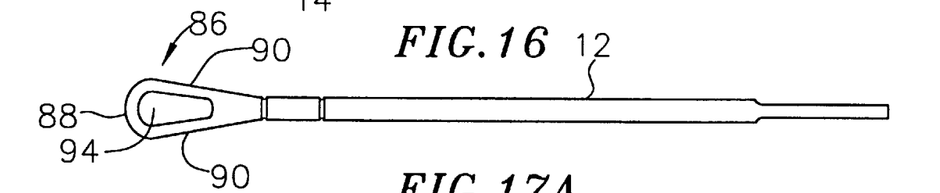
FIG. 16 is a top view of a alternative embodiment cutting device having a rounded style entry tip configuration.
Figure 19A:
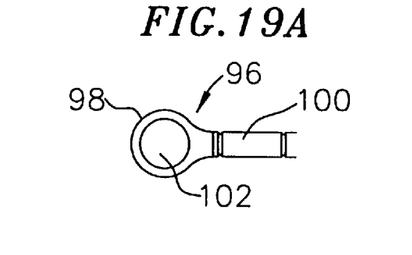
FIG. 19a is a top view of a round cutting head configuration of the cutting device.
Figure 19B:
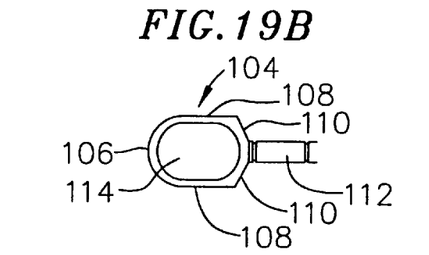
FIG. 19b is a top view of a bulb cutting head configuration of the cutting device.
Figure 20:
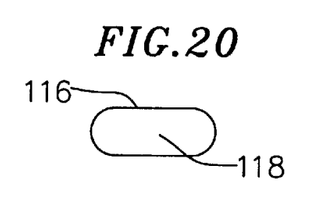
FIG. 20 is an end view of the cutting head of FIG. 19b having a rounded style entry tip configuration.

The geometrical shape of the cutting head can also be varied. The cutting head 16 of the cutting device embodiments referenced herein illustrate a generally elliptical cutting head. Alternative cutting head geometries can be seen in FIGS. 16, 19A and 19B. FIG. 16 illustrates a tear drop cutting head configuration 86 having a rounded entry tip 88 and includes converging walls 90 extending from entry tip 88 to main shaft 92. In the tear drop configuration the cutting head includes a tear drop shaped window 94. FIG. 19a illustrates a round cutting head configuration 96. In this configuration the cutting head includes a rounded outer wall 98 extending from the main shaft 100. The round cutting head also includes a circular window 102. FIG. 19b illustrates a bulb cutting head configuration 104 having a rounded entry tip 106 and generally parallel side walls 108. Converging back walls 110 extend from the main shaft 112 to the parallel side walls 108. The bulb cutting head configuration includes a generally elliptical or oval window 114. In each of the tear drop cutting head configuration, round head configuration, and bulb head configuration, the entry tips have a rounded configuration as shown in FIG. 20. The rounded entry tip includes an oval perimeter 116, and a rounded outer surface 118.

Figure 21A:
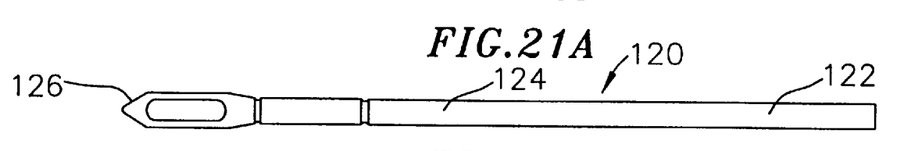
FIG. 21a is a top view of a cervical version of the cutting device.
Figure 21B:
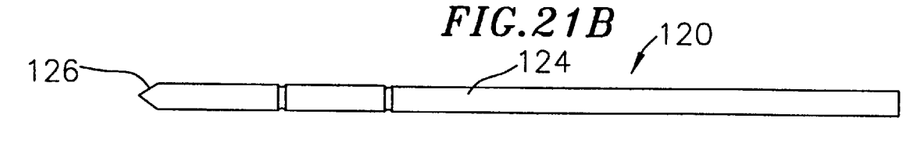

FIGS. 21A and 21B illustrate a cervical cutting device 120 wherein the mounting shaft 122 and main shaft 124 are of equal diameter. The cervical cutting tool preferably would have an overall length of 3.75 inches and a cutting head diameter of 0.125 to 0.160 inches. As seen in FIG. 21B, the height of the cutting head 126 is equal to the diameter of the main shaft.

Figure 22:
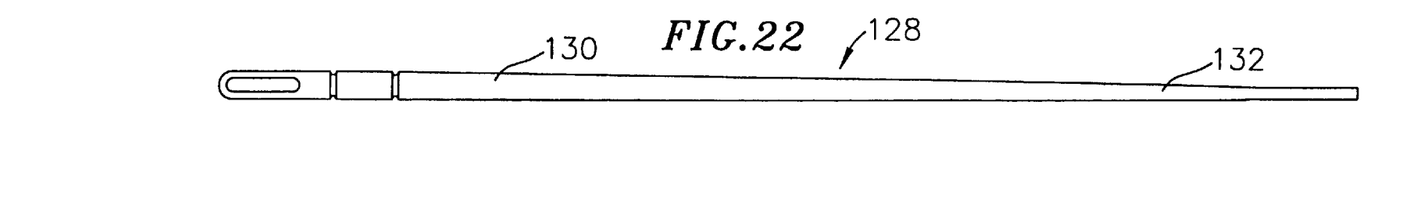
FIG. 22 is a top view of a cutting device illustrating an alternate tapered shaft configuration.
Figures 23, 24:
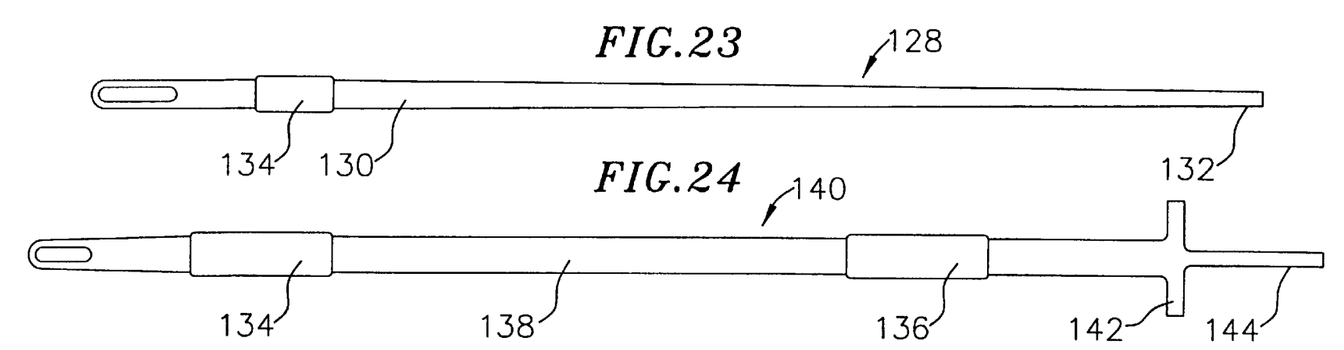
FIG. 23 is a side view of the cutting device of FIG. 22 including a bearing or bushing.
FIG. 24 is a side view of a cutting device including multiple bearings and a mechanical depth stop.

FIGS. 22 and 23 illustrates yet another alternative cutting device 128 having a tapered main shaft 130 without fillets at the juncture between the main shaft and the mounting shaft 132. Cutting device 128, by having a tapered main shaft, provides a design having improved strength and rotational stability for longer shaft lengths. Longer shaft length cutting devices are particularly useful when the cutting device is used in conjunction with a cannula.

When the cutting device is used with a cannula, a bushing or bearing 134 is placed along the main shaft 130 to reduce the friction between the main shaft and the cannula into which the cutting device is inserted. If a bushing is used, it is preferably made from metal or plastic. If a bearing were used, it would be a ball or race type bearing. Multiple bearings or bushings 134 and 136 can be utilized along the main shaft 138 of a cutting device 140 as shown in FIG. 24. Although two bearings or bushings 134 and 136 are shown, it is to be understood that any multiple number of bearings or bushings having varying lengths can be positioned along the main shaft of the cutting device to reduce friction between the cutting device and a cannula.

Figure 25:
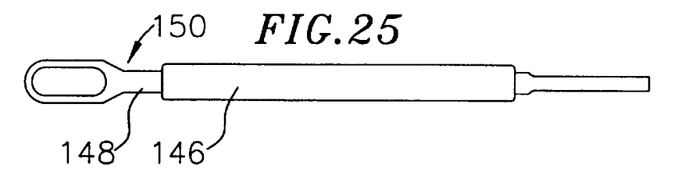
FIG. 25 is a side view of a cutting device including a full length bearing or bushing.

A mechanical depth stop 142 can be incorporated into the cutting device typically at the juncture between the main shaft 138 and the mounting shaft 144 to prevent the cutting device from extending too far from the end of the cannula (see FIG. 26) when in use. Alternatively, instead of utilizing one or multiple bearings or bushings, a full length bushing or bearing 146 can be positioned on the main shaft 148 of a cutting device 150 as shown in FIG. 25.

Figure 26:
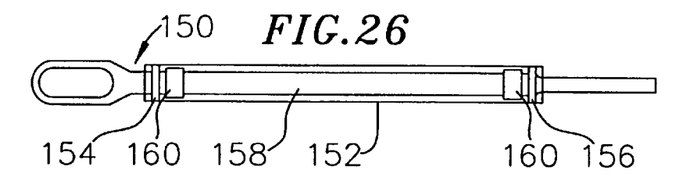
FIG. 26 is a cross-sectional side view of a cutting device captive within a cannula.

The cutting device 150 can be removable from the cannula 152 or can be captive within the cannula as shown in FIG. 26. When in a captive configuration, the cannula 152 (or a surgical guard in other applications) includes retainer rings 154 and 156 at opposite ends of the main shaft 158 to rigidly secure the cannula to the main shaft. Two bearings or bushings 160 are positioned within the cannula, however it is to be understood that the number and length of each bearing or bushing can vary for the particular application.

Figure 27:
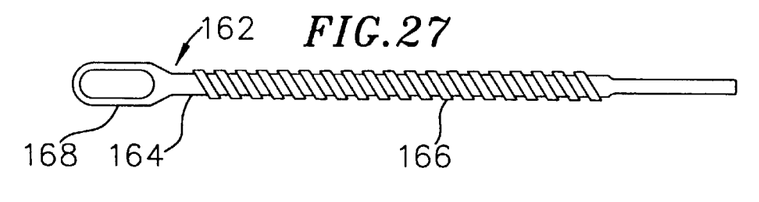
FIG. 27 is a cutting device with a screw shaft.

FIG. 27 illustrates an alternative embodiment main shaft configuration for a cutting device 162. The main shaft 164 is threaded 166, which assists in moving displaced emulsified disk material from the cutting head, up the main shaft 164 and away from the surgical site. Although cutting device 162 is only shown in FIG. 27, it is to be understood that device 162 is used in conjunction with a cannula or drill guard as shown in FIG. 26 for device 150. The threads 166 move the removed tissue along the shaft 164 within the cannula or drill guard.

Figure 28:
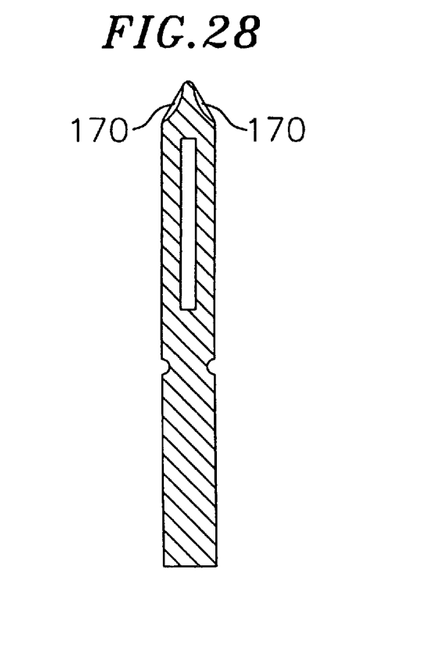
FIG. 28 is a cross-sectional side view of a modified arrow tip cutting head configuration taken along line 28—28 of FIG. 28A.
Figure 28A:
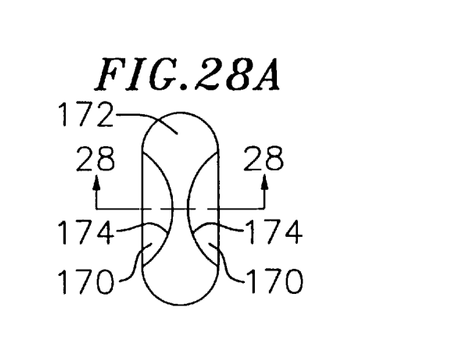
FIG. 28A is an end view of the cutting head of FIG. 28.
Figure 29:
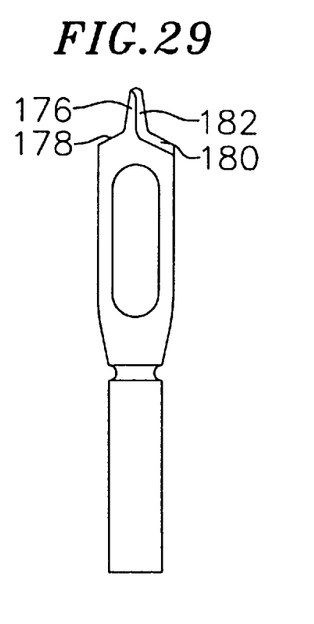
FIG. 29 is a top view of an auger tip cutting head configuration of the cutting device.
Figure 29A:
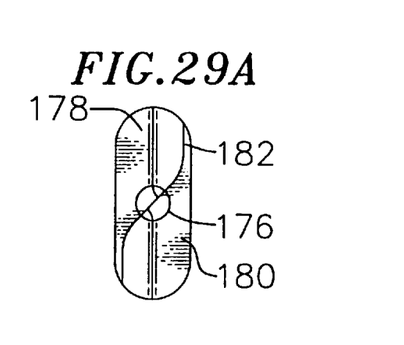
FIG. 29A is an end view of the cutting head of FIG. 29.
Figure 30:
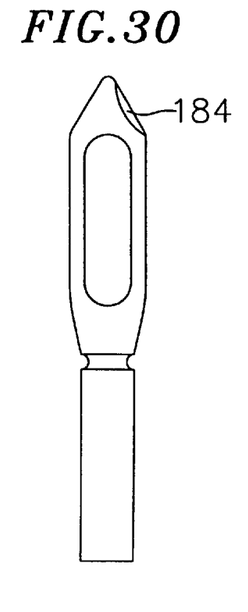
FIG. 30 is a top view of an additional modified arrow tip cutting head configuration.
Figure 30A:
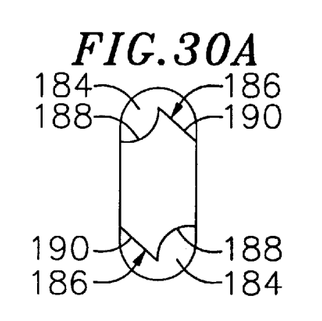
FIG. 30A is an end view of the cutting head configuration of FIG. 30.

FIGS. 28 through 36 illustrate additional cutting head configurations for the cutting device. FIG. 28 illustrates a modified arrow tip cutting head configuration wherein semi-circular portions 170 are removed from the entry tip, thereby defining semi-circular cutting blades 174 positioned on either side of the entry tip 172. Cutting blades 174 on the entry tip provide a smoother entry into the intervertable disk space and a more rapid removal of matter. FIGS. 29 and 29A illustrate an auger tip cutting head configuration wherein the entry tip includes a narrow pyramidal entry portion 176 and angled base portions 178 and 180. A blade 182 is machined onto the leading edge of the pyramidal center portion 176. Blade 182 also provides a smoother entry into the intervertabral disc space and rapid removal of matter. FIG. 30 illustrates a second modified arrow tip configuration in which a semi-circular and angled portion 184 is removed from each end of the entry tip to form a cutting blade 186 having a semi-circular portion 188 and an angled relief portion 190. Semi-circular and angled portion 184 provide a more aggressive cutting action for the cutting device.

Figures 31, 32:
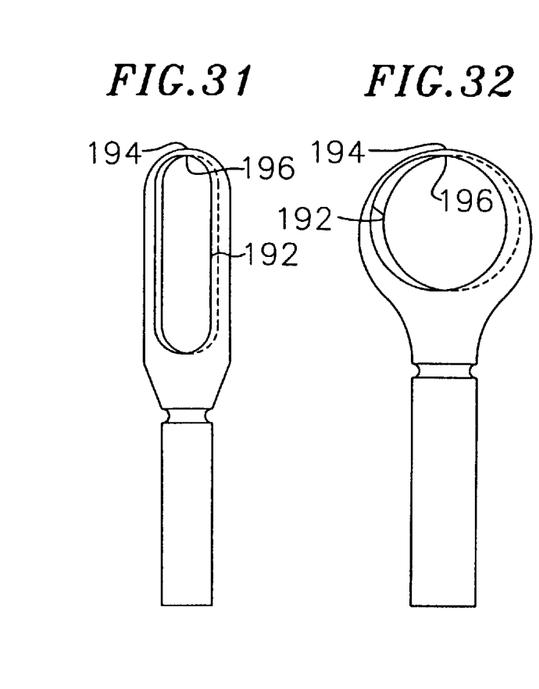
FIG. 31 is a top view of a modified elliptical cutting head configuration.
FIG. 32 is a top view of a modified rounded cutting head configuration.

FIGS. 31 and 32 illustrate modified elliptical and round cutting head configurations, respectively wherein the window 192 has been raised so that the window 192 forms a thin portion 194 along the upper perimeter of the entry tip thereby extending the cutting blade around the upper perimeter 196 in the window. By moving the window upwardly, the cutting blade is not limited to just the sides of the window and allows for the easy removal of disc material using a lateral movement of the cutting device across the intervertabral disc space.

Figure 33:
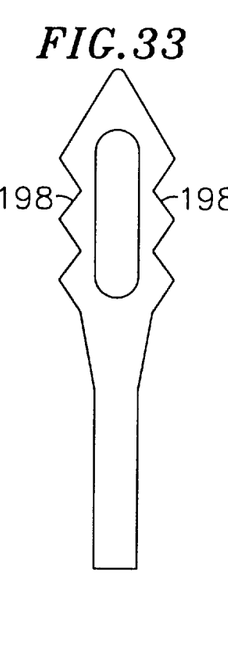
FIG. 33 is a top view of a notch cutting head configuration.
Figure 34:
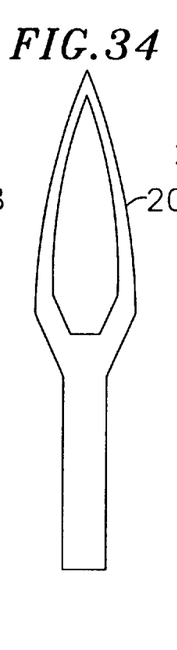
FIG. 34 is a top view of a flame cutting head configuration.
Figure 35:
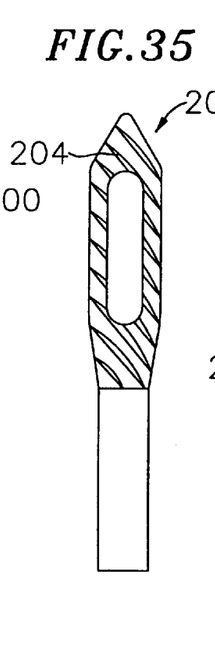
FIG. 35 is a top view of a fluted cutting head configuration.
Figure 36:
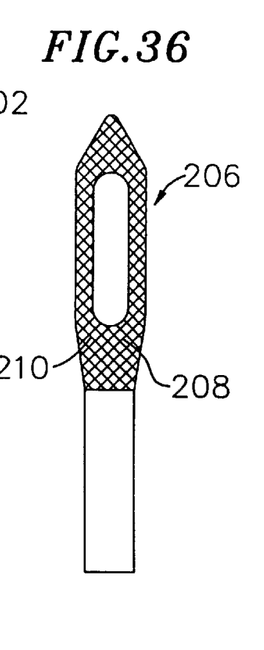
FIG. 36 is a top view of a rasp cutting head configuration.

FIG. 33 illustrates a notched cutting head configuration wherein each side of the cutting head includes serrations 198. FIG. 34 illustrates a flame shaped cutting head configuration 200. FIG. 35 illustrates a fluted cutting head configuration 202 wherein the cutting head includes raised spiral flutes or helixes 204 circling the diameter of the head. FIG. 36 illustrates a rasp cutting head configuration 206 wherein the cutting head is knurled producing smaller flutes 208 and 210 crisscrossing in both directions around the diameter of the cutting head. The cutting head configurations of FIGS. 33 through 36 allow for the easy removal of matter using a lateral movement of the cutting head across the intervertabral disc space, and in particular the flutes of FIGS. 35 and 36 provide for the head to be more aggressive in the removal of material. Additionally, any of the cutting head configurations depicted herein can be diamond coated by dipping the cutting heads into a diamond emulsion to enhance the cutting capabilities of the device.

Although the present invention has been described and is illustrated with respect to various embodiments thereof, it is to be understood that it is not to be so limited, since changes and modifications may be made therein which are within the full intended scope of the invention as hereinafter claimed.

What is claimed is:

1. A cutting device for removing matter from a surgical site during a surgical procedure comprising:
    means for emulsifying the matter during the surgical procedure;
    said emulsifying means including an entry tip portion having at least one cutting blade positioned on an outer closed surface of the entry tip portion and a body portion having a cutting blade disposed each of on opposed leading edges of a window extending through the body portion such that each cutting blade of the body portion faces in the same direction of rotation, the cutting blades of the body portion being substantially stationary relative to each other; and
    means for rotatably supporting the emulsifying means during the surgical procedure.

2. The cutting device of claim 1 wherein the window in the emulsifying means defines two walls extending at an angle from each cutting blade.

3. The cutting device of claim 2 wherein the walls extend at an angle from about 15° to about 30° from a horizontal plane extending perpendicular to an opening of the window.

4. The cutting device of claim 1 wherein the emulsifying means is a generally elliptically shaped cutting head.

5. The cutting device of claim 1 wherein the cutting blade on the entry tip portion is semi-circular.

6. The cutting device of claim 1 wherein the cutting blade on the entry tip portion is a raised spiral flute circling a diameter of a cutting head of the emulsifying means.

7. The cutting device of claim 1 wherein there are a plurality of cutting blades on the entry tip portion, and the cutting blades are criss-crossing spiral flute s circling a diameter of a cutting head of the emulsifying means.

8. The cutting device of claim 1 wherein the support means comprises a main shaft and a mounting shaft.

9. The cutting device of claim 8 wherein the main shaft is threaded.

10. The cutting device of claim 8 further comprising means for protecting an area adjacent the surgical site.

11. The cutting device of claim 10 wherein the means for protecting an area adjacent the surgical site is a cannula.

12. The cutting device of claim 11 further comprising means for reducing friction between the main shaft and the cannula.

13. The cutting device of claim 12 wherein the means fir reducing friction is at least one bushing.

14. The cutting device of claim 12 wherein the means for reducing friction is at least one bearing.

15. The cutting device of claim 10 wherein the means for protecting an area adjacent the surgical site is a drill guard.

16. The cutting device of claim 10 wherein the support means includes a depth stop to prevent the main shaft from protruding from the means for protecting the area adjacent the surgical site.

17. The cutting device of claim 1 wherein the emulsifying means is a serrated cutting head.

18. The cutting device of claim 1 wherein the emulsifying means is a generally flame shaped cutting head.

19. The cutting device of claim 1 wherein the cutting blades of the body portion are independent of the cutting blade of the entry tip portion.

20. The cutting device of claim 1 wherein the support means includes a shaft connected to the emulsifying means.

21. The cutting device of claim 20 wherein the cutting blades are fixedly connected to the shaft.

22. A surgical cutting device for emulsifying matter from a surgical site comprising:
    a cutting head defining an axis of rotation about which the cutting head rotates, the cutting head having an entry tip portion and a cutting blade on each of opposed leading edges of a window extending through an interior portion of the cutting head wherein each cutting blade faces in the same direction of rotation, each of the cutting blades extending in general parallel relation to the axis along at least a major portion of the length thereof;
    a shaft connected to the cutting head for mounting the cutting head to a rotary surgical drill; and
    means for protecting the surgical site from inadvertent emulsification.

23. The cutting device of claim 22 wherein the window in the cutting head includes two walls extending at an angle from each of the cutting blades.

24. The cutting device of claim 22 wherein the protection means is a cannula positioned around the shaft.

25. The cutting device of claim 22 wherein the protection means is a drill guard extending from the rotary surgical drill around the shaft.

26. The cutting device of claim 22 further comprising at least one bushing on the shaft.

27. The cutting device of claim 22 further comprising at least one bearing on the shaft.

28. The cutting device of claim 22 wherein the shaft includes a depth stop.

29. The cutting device of claim 22 wherein the shaft is threaded.

30. The cutting device of claim 22 wherein the entry tip portion of the cutting head defines a cutting edge independent of the cutting blade.

31. A surgical apparatus for cutting tissue, which comprises:

an elongated shaft having proximal and distal ends and defining a longitudinal axis, the elongated shaft adapted for rotational movement about the longitudinal axis; and a cutting head disposed adjacent the distal end of the elongated shaft and adapted for rotational movement therewith, the cutting head having first and second cutting elements arranged about the longitudinal axis to define a window therebetween, the cutting elements each defining a leading cutting edge dimensioned and configured to cut tissue upon rotation of the cutting head in a first rotational direction and to generally direct tissue portions cut thereby into the window whereby the cut tissue portions are at least partially emulsified upon continued rotation of the cutting head, the cutting head further including an entry tip portion disposed distal of the cutting elements, the entry tip portion defining an entry cutting edge dimensioned to facilitate entry of the cutting head within the tissue.

32. The surgical apparatus of claim 31 wherein the cutting edges of the cutting elements are in general parallel relation with the longitudinal axis of the elongated shaft.

33. The surgical apparatus of claim 31 wherein the cutting elements and the entry tip portion are the sole cutting elements of the cutting head.

34. The surgical apparatus of claim 31 wherein the entry cutting edge of the entry tip portion is independent of the leading cutting edges of the cutting elements.

35. The surgical apparatus of claim 31 wherein the elongated shaft includes a groove defined in an outer surface thereof dimensioned to convey tissue removed by the cutting head in a proximal direction.

36. The surgical apparatus of claim 31 wherein the cutting edges of the cutting elements are dimensioned and configured to cut intervertebral disc tissue.

37. The surgical apparatus of claim 31 including a cannula defining longitudinal opening and wherein the elongated shaft is at least partially disposed in the longitudinal opening of the cannula.

38. The surgical apparatus of claim 31 wherein the entry tip portion defines a closed end face.

* * * * *